United States Patent [19]

Flickinger et al.

[11] Patent Number: 5,426,052
[45] Date of Patent: Jun. 20, 1995

[54] BACILLUS MGA3 DIAMINOPIMELATE DECARBOXYLASE GENE

[75] Inventors: Michael C. Flickinger, St. Paul; David A. Mills, Minneapolis, both of Minn.

[73] Assignee: Regents of the University of Minnesota, Minneapolis, Minn.

[21] Appl. No.: 698,926

[22] Filed: May 10, 1991

Related U.S. Application Data

[63] Continuation-in-part of Ser. No. 673,263, Mar. 20, 1991, abandoned, which is a continuation of Ser. No. 351,436, May 12, 1989, abandoned, and a continuation-in-part of Ser. No. 673,264, Mar. 20, 1991, which is a continuation of Ser. No. 335,691, Apr. 10, 1989, abandoned.

[51] Int. Cl.$^6$ ............... C07H 21/04; C12N 9/88; C12N 15/60; C12R 1/07
[52] U.S. Cl. ................. 536/23.2; 435/320.1; 435/232; 435/832
[58] Field of Search ............ 435/232, 252.5, 320.1, 435/832; 536/27, 23.2, 23.7, 24.1, 24.32

[56] References Cited

U.S. PATENT DOCUMENTS 3,707,441 12/1972 Shiio et al. .................. 195/29
4,652,527 3/1987 Stirling ..................... 435/244

OTHER PUBLICATIONS

Cremer, J. et al. *J. Gen. Microbiol.* 134:3221-3229 (1988).
Asada, Y. et al. *Biochemistry* 20:6881-6886 (1981).
Suggs, S. V. et al. *PNAS* 78:6613-6617 (1981).
Yamamoto, J. et al. *Nucleic Acids Research* 17:10105 (1989).
Guettler, M. et al. Asm Abstract 1-95 (1988). p. 196.
O. Tosaka et al., *Trends in Biotechnology*, 1, 70 (1983).
F. Schendel et al., *Appl. Environ. Microbiol.*, 56, 963 (1990).
N. Al-Awadhi et al., *Biotechnol. Bioeng.*, 36, 816 (1990).
H. Hagino et al., *Biotechnol. Lett.*, 3, 425 (1981).
P. White et al., *Biochem. J.*, 96, 75 (1965).
C. Martin et al., *FEMS Micro. Lett.*, 36, 105 (1986).
A. Rosner, *J. Bacteriol.*, 121, 20 (1975).
A. Bukhari et al., *J. Bacteriol.*, 105, 844 (1971).
H. Birnboim et al., *Nucl. Acids Res.*, 7, 1513 (1979).
R. Yasbin et al., *J. Bacteriol.*, 121, 296 (1975).
J. Langridge et al., *Anal. Biochem.*, 103, 264 (1980).
F. Sanger et al., *Proc. Natl. Acad. Sci. USA*, 74, 5463 (1977).
M. Biggin et al., *Proc. Natl. Acad. Sci. USA*, 80, 3963 (1983).
J. Kelland et al., *Biochemistry*, 24, 3263 (1985).
O. Lowry, *J. Biol. Chem.*, 193, 265 (1951).
Y. Asada et al., *Agric. Biol. Chem.*, 45, 1513 (1981).
P. Andrews, *Biochem. J.*, 91, 222 (1965).
P. Matsudaira, *J. Biol. Chem.*, 262, 10035 (1987).
A. Bartlett et al., *J. Gen. Microbiol.*, 131, 2145 (1985).
T. Akiba et al., *J. Ferment. Technol.*, 48, 323 (1970).
N. Al-Awadhi et al., *Appl. Microbio. Biotechnol.*, 29, 485 (1988).
C. Anthony, *Biochemistry of Methylotrophs*, Academic Press, London, p. 3 (1982).
L. Band et al., *DNA*, 3, 17 (1984).
A. Brooke et al., *Arch. Microbiology*, 151, 268 (1989).
R. Cox et al., *Biochem. J.*, 141, 605 (1974).
G. de Vries, *FEMS Microbiology Reviews*, 39, 235 (1986).
G. de Vries et al., *FEMS Microbiology Review*, 75, 57 (1990).
L. Dijkhuizen et al., *FEMS Microbiology Letters*, 52, 209 (1988).
M. Guettler et al., *ASM Annual Meeting* (1988).
C. Haber et al., *Science*, 221, 1147 (1983).

(List continued on next page.)

*Primary Examiner*—Robert A. Wax
*Assistant Examiner*—Dian C. Jacobson
*Attorney, Agent, or Firm*—Merchant, Gould, Smith, Edell, Welter & Schmidt

[57] ABSTRACT

The present invention provides the isolated DNA sequence enclocking the dimer subunit of the lysine-sensitive diaminopimelate decarboxylase from the thermophilic methylotrophic *Bacillus sp.* MGA3.

2 Claims, 6 Drawing Sheets

OTHER PUBLICATIONS

R. Hanson, *Adv. Applied Microbiology*, 26, 3 (1980).
N. Harms et al., *J. Bacteriology*, 169, 3969 (1987).
B. Holloway, *Methylotrophs: Microbiology, Biochemistry and Genetics*, C. T. Hou, ed., CRC Press, Boca Raton, Fla., pp. 1–39 (1984).
B. Holloway et al., in *Microbial Growth on $C_1$ Compounds*, H. W. Van Verseveld and J. A. Duine, eds., Martinies Nyhoff, Dordrecht, pp. 223–229 (1987).
M. Katinka et al., *Proc. Nat'l. Acad. Sci. USA*, 77, 5730 (1980).
R. Kolter et al., *Ann. Rev. Genet.*, 16, 113 (1982).
T. Kunkel, *Proc. Nat'l. Acad. Sci. USA*, 82, 488 (1985).
U. Laemmli, *Nature*, 227, 680 (1970).
P. Large et al., *Methylotrophy and Biotechnology. Longman Scientific and Technical*, John Wiley and Sons, New York, pp. 146–162 (1988).
G. Lee et al., *Mol. Gen. Genet.*, 180, 57 (1980).
J. Linton et al., in *Microbial Growth on $C_1$ Compounds*, H. W. Van Verseveld and J. A. Duine, eds., Martinies Nyhoff, Dordrecht, pp. 263–271 (1987).
A. Mimura et al., *J. Ferment. Technol.*, 56, 243 (1978).
C. Moran, Jr. et al., *Mol. Gen Genet.*, 186, 339 (1982).
F. Schendel et al., *1989 ASM Annual Meeting* (Poster Session).
I. Shiio, *Biotechnology of Amino Acid Production*, K. Aida, I. Chibata, K. Nakayama, K. Takinami, and H. Yamada, eds., pp. 188–206 (1983).
H. Shimotsu et al., *J. Bacteriol.*, 166, 461 (1986).
B. Snedecor et al., *Applied Microbiology*, 27, 1112 (1974).
O. Tosaka et al., *Biotechnology of Amino Acid Production*, K. Aida, I. Chibata, K. Nakayama, K. Takinami, and H. Yamada, eds., pp. 152–172 (1983).
R. Whittenbury et al., *J. General Microbiology*, 61, 219 (1970).
C. Wolff et al., *J. Bacteriol.*, 170, 4509 (1988).
F. Schendel et al., *1990 ASM Annual Meeting* (Poster Session).
D. Mills et al., *1990 ASM Annual Meeting* (Poster Session).

FIG. 3A

```
    CGG GTC AAA AAT ACG CCC AAG CAT CAT TCA TAC AAA AAA TCG ATA CCG CCA ACC
    GAC ATA AGA AAA GCA GAA GCA TTA TGC AAC TTG AAT CAA TTG CGA ATT TTC AAA
    TCT TAT GGT AAG TTT TTT GTT ATT AAA GAA TCC ATT AAA GGG CAG AAA TCA ATA
    CCT ACT TGA AAG ATT CTA TTC ATT TGT TTA TAT TCA AAA TAA TTC ATT TTT AAT
                                                           RBS                   +1
    AAA TAT TCG GGA TCG ACA TAT TGA GTG ATA AGG GGA ATG ACA GAA ATG TAT
                                                              M   T   E   M   Y
  7 TTT CAT GGC ACA ACA AAG GTA AAT GAA AAG GGA CAT TTA GAA ATC GGC GGA GTG
    F   H   G   T   T   K   V   N   E   K   G   H   L   E   I   G   G   V
 61 GAT ACG ATC GAA CTT GCA CAA AAG TAT GGC ACG CCT CTA TAT GTA TAC GAC GTT
    D   T   I   E   L   A   Q   K   Y   G   T   P   L   Y   V   Y   D   V
115 GCT TTA ATT CGC GAG CGG GCT AGA GGG TTT AAA AAT ACG TTT GAT GAG CTT GGT
    A   L   I   R   E   R   A   R   G   F   K   N   T   F   D   E   L   G
169 ATT AAA GCT CAA GTT GCA AGC TAT GCA AAA TTT TCT ACA GTA GCA ATG ATT
    I   K   A   Q   V   A   S   Y   A   K   F   S   T   V   A   M   I
223 CAG CTT GCA GAA GAG GAA GGC TTG TCA CTG GAT GTT GTA TCA GGC GGA GAG CTT
    Q   L   A   E   E   E   G   L   S   L   D   V   V   S   G   G   E   L
```

```
277 TAT ACA GCT TTG GTC GCA GGT TTC CCT GTT CAT AAA ATC CAT TTT CAT GGT AAT
     Y   T   A   L   V   A   G   F   P   V   H   K   I   H   F   H   G   N
331 AAT AAA AGC AGA GCC GAA CTG GAA ATG GCA TTG GAG CAC CAA ATA GGC TGC ATT
     N   K   S   R   A   E   L   E   M   A   L   E   H   Q   I   G   C   I
385 GTT GAT AAT TTT CAT GAA CTT GAT CTT ATT GAT TCC ATA TGT TCC GAA AAG
     V   V   D   N   F   H   E   L   D   L   I   D   S   I   C   S   E   K
439 AAT GTA AAA ACA AAT ATT CTT TTG AGA GTA ACT CCA GGA ATT GAG GCT CAT ACG
     N   V   K   T   N   I   L   L   R   V   T   P   G   I   E   A   H   T
493 CAT GAC TAT ATT TTA ACG GGG CAG GAA GAC TCT AAG TTT GGG TTT GAC CTT CAA
     H   D   Y   I   L   T   G   Q   E   D   S   K   F   G   F   D   L   Q
547 AAC GGC CAG GCT GAA AAA GCA CTT CAA ATT GCG TTA AAT TCA AAC TTT GTT GAA
     N   G   Q   A   E   K   A   L   Q   I   A   L   N   S   N   F   V   E
601 GTT CTC GGG GTT CAC TGC CAT TGC ATT GGT TCA CAA ATT TTT GAT ACT ACC GGA TTT
     V   L   G   V   H   C   H   C   I   G   S   Q   I   F   D   T   T   G   F
655 GTT CTA GCA GCA AGA AAA ATC TTT GAA AAA TTA AAG GAA TGG AAA GAT AGG CTG
     V   L   A   A   R   K   I   F   E   K   L   K   E   W   K   D   R   L
709 TCA TAC GAG CCA AAA GTA TTA AAT CTT GGA GGC GGA TTC GGA ATT CGT TAT ACA
     S   Y   E   P   K   V   L   N   L   G   G   G   F   G   I   R   Y   T
763 GAG GAA GAT GAT CCT ATT CCA GCA TCT CAA TAT GTG AAA GAA ATT ATT AAC GAA
     E   E   D   D   P   I   P   A   S   Q   Y   V   K   E   I   I   N   E
```

FIG. 3B

```
817  GTG AAA AAA CAA GTA TCC GCT TAT TCC ATG AAA ATG CCT GAA ATT TGG ATT GAA
      V   K   K   Q   V   S   A   Y   S   M   K   M   P   E   I   W   I   E

871  CCT GGG CGT TCT CTT GGT GAT GCT GGA ACA ACA TAT CAG ATC GGT TCT
      P   G   R   S   L   V   G   D   A   G   T   T   Y   Q   I   G   S

925  AGG AAA GAT GTC CCA AAC GTG AGG CAT TAT GTG GCT GTA GAC GGA GGT ATG AGT
      R   K   D   V   P   N   V   R   H   Y   V   A   V   D   G   G   M   S

979  GAC AAT ATC CGC GCT CCC GCT TTG TAC AAT GCT AAG TAT GAA GCT GTA TTG GCA AAT
      D   N   I   R   A   P   A   L   Y   N   A   K   Y   E   A   V   L   A   N

1033 AAA CCA CTT GCG AAA GCG GAT GAA ACA GTT TCA ATT CCT CTT AAA GCA GGC AAG TGC TGT GAA
      K   P   L   A   K   A   D   E   T   V   S   I   P   L   K   A   G   K   C   C   E

1087 TCA GGA GAT ATG CTT ATA TGG GAT TTG CCT TAT GGT CAT GCG AAT GCA ATG GAC AGT GAT GAT
      S   G   D   M   L   I   W   D   L   P   L   P   K   A   D   S   D   D

1141 ATA CTT GCT GTC TTT TGT TTT ACC GGA GCA TAT GGT GTT GAG TCA ATG GCA AAT AAT TAT
      I   L   A   V   F   C   F   T   G   A   Y   G   V   F   E   V   S   M   A   N   N   Y

1195 AAC CGG ATT CCA AGG CCG GCC ATG GTA TTT GTT GAG AAT GGG GAA TCA ATG CTT
      N   R   I   P   R   P   A   M   V   F   V   E   N   G   E   S   M   L

1249 GTA GTG AAA CGG AAA CAT ATG AGG ACC TCG TCC GCA ATG ATC TGC CTT TAA AAG
      V   V   K   R   K   H   M   R   T   S   S   A   M   I   C   L   *
```

FIG. 3C

```
1303 AAA GAG TAA GAT ACT AAG CTG CCG GTT CTC GGC AGC TTA GTT ACT AGA AGA TGG
1357 ATT AAA AAT GCA TTT TAG TGT AGA ATT AGG AAC AGC TTA TTG TTT ATA TTA TAG
1411 GCT GGG AGG ATC TGA TTC ATT TAT GAA AAA AGA AAA TTG GTT GGT GTT TTC TTT
1465 TAT TCT TGT CAT GTC GCT ATG GGG ATG TTT CTA TTG GTT CTT TAT TGC TGC GCC
1519 TAT ACA ATG ATA TAA AAT GAC CTT GAC AAG AAA TTG AAG AAT TGC CAT CAT TTT
1573 TAT ATG ATA AGG TCA ATT ACT AGA CAC GCC ATA TTC AAC ATA TAC TAA
1627 ATG TCA AAG TTC ATA AAT TGG TGA ACA AAG TTC GAA TTC ATT AAT GAG GGA TTT
1681 TCA GTA TGT TAA TAC GTT ATA AGA AAG CAT TTG AAA AAC TTC AGC TGA GAC AGC
1735 TAT CCT TTA TGC CAA ATG AGA AGG ATT TGA AGA AAC TTC GGA AGG AAG ATA
1789 AGT ATG AAA CCG AAG AAG ACC GAC AGT TGT TTC TGT AAT ACG AAG TCG TAC ATC
1843 TTA TCG GCC TTA TAG GTG TAC TTG TTA ATG ATC CAC ATC GTC AAG GTA AGA TGG TAA
1890 ATA TAT CTG TTA ACC CTT CAC ATC CTG ATA TTT GTC ATG ATA AAG GCA AGA TGG TAA ATA CAG
1951 AGG CAT TAA GAG ATA TTT ATC CTG ATA AAG AGC TGA TAC CAA ATG AAA ATA CAG
2005 CGG CTT TCA TAG AAA AAT GTG AGA TTT GTC ATG AAT AAT GAT TAT TCG
2059 CTG CCT TTT TTC TTT CGA TTG ATC ATT GCA ATT TCC GTT CTT TAT G
```

FIG. 3D

BACILLUS MGA3 DIAMINOPIMELATE DECARBOXYLASE GENE

CROSS REFERENCE TO RELATED APPLICATION

This application is a Continuation-in-Part of U.S. patent application Ser. No. 07/673,263, filed Mar. 20, 1991, now abandoned, which is a Continuation of U.S. patent application Ser. No. 07/351,436, filed May 12, 1989, now abandoned. U.S. patent application Ser. No. 07/673,263 is in turn a Continuation-in-Part of U.S. patent application Ser. No. 07/673,264, filed Mar. 20, 1991, which is a Continuation of U.S. patent application Ser. No. 07/335,691, filed Apr. 10, 1989, now abandoned.

BACKGROUND OF THE INVENTION

As shown in FIG. 1, diaminopimelate (DAP) decarboxylase, (EC 4.1.1.20), acts in the last step in the lysine biosynthetic pathway, by catalyzing the decarboxylation of meso-diaminopimelate to lysine. In bacteria, DAP decarboxylase plays a crucial role in balancing two essential metabolites; meso-DAP, a component of cell wall peptidoglycan (and a spore wall component), and the amino acid lysine, used for protein production. DAP decarboxylases isolated from both plants and bacteria have a strict requirement for pyridoxal-phosphate (PLP) as a cofactor. DAP decarboxylase is the only PLP-dependent alpha-decarboxylase known to work on a D-amino acid.

Commercially, L-lysine is primarily used as a supplement for animal feeds derived from grains that contain only limited quantities of this amino acid. Poultry, swine, and other livestock are unable to synthesize L-lysine and therefore must have this amino acid supplied as part of their diet. Currently, L-lysine is manufactured by either direct fermentation or enzymatic conversion of DL-α-amino-ε-caprolactam. Fermentation processes using strains of *Corynebacterium glutamicum* or *Brevibacterium lactofermentum* have become the major methods for L-lysine production. (O. Tosaka et al., *Trends in Biotechnology*, 1, 70 (1986)).

Recently, F. J. Schendel et al. in *J. Appl. Environ. Microbiol.*, 56, 963 (1990), identified homoserine auxotrophs and S-(2-aminoethyl)-cysteine (AEC) resistant mutants of a thermophilic methylotrophic *Bacillus sp.* which overproduce significant quantities of L-lysine at 50° C. Such thermophilic methylotrophs may have advantages over other organisms for industrial use, as discussed by Al-Awadhi et al., *Biotechnol. Bioeng.*, 36, 816, 821 (1990). In particular, the methylotrophic Bacillus MGA3 identified by F. J. Schendel et al., cited supra, may have significant advantages over other *bacilli* for the overproduction of lysine since it does not sporulate at high temperatures even under conditions of nutrient limitation, in contrast to lysine-producing mutants of *B. licheniformis* that sporulated when grown at temperatures greater than 40° C. (H. Hagino et al., *Biotechnol. Lett.*, 3, 425 (1981)).

Since both spore components, diaminopimelate and dipicolinic acid, are derived from the lysine biosynthetic pathway, as shown in FIG. 1, differences in the regulation of this pathway may occur between this thermophilic *Bacillus sp.* and other mesophilic *bacilli*. Therefore, a need exists to isolate and characterize the informational macromolecules (DNA and RNA) which function in the biosynthetic pathway to lysine, methionine and threonine in the thermotolerant *Bacillus sp.* MGA3. A further need exists to isolate and characterize the products, such as the enzymes, that function in these biosynthetic pathways. A further need exists to produce mutant varieties of said informational macromolecules, in order to improve the properties of the enzymes and other polypeptides encoded thereby, or to produce improved strains of thermophilic, methylotrophic bacteria.

SUMMARY OF THE INVENTION

The present invention provides a DNA sequence in substantially pure form, which corresponds to the structural gene coding for the dimer subunit of lysine-sensitive diaminopimelate (DAP) decarboxylase of the methylotrophic thermotolerant *Bacillus sp.* MGA3. For brevity, this gene can be referred to as the Bacillus MGA3 lysA gene, and is shown in SEQ. I.D. No. 1.

The DNA sequence was identified by cloning the lys A structural gene from a genomic library via complementation of an *Escherichia coli* auxotrophic mutant lacking DAP decarboxylase ("lysA 22") as summarized in FIG. 2. The nucleotide sequence of the entire 2.3 Kb PstI fragment has been determined to be as depicted in FIG. 3 and a single open reading frame coding for the about 50 kD enzyme subunit was identified at positions 265–1560 of this fragment.

The present invention also provides a substantially pure enzyme corresponding to this form of DAP decarboxylase and a substantially pure polypeptide corresponding to the dimer subunit of DAP decarboxylase. DAP decarboxylase is a dimer ($M_r$ 86,000). The N-terminal sequence was found to be identical with those predicted from the gene sequence. The predicted sequence of 432 amino acids (SEQ. I.D. No. 2) shows some sequence homology with the sequence of *B. subtilis* DAP decarboxylase.

Availability of the MGA3 DAP decarboxylase gene, coupled with knowledge of its sequence, permits the production of mutant forms of the present DAP decarboxylase, via mutagenesis of the gene. Mutant forms of the DAP decarboxylase gene may be useful to produce microorganisms such as new strains of bacteria, which overproduce lysine at higher levels, or under even more stringent environmental conditions. Methodologies for the mutagenesis of the DAP decarboxylase gene are known to the art, as discussed in detail in U.S. patent application Ser. No. 07/684,135, filed Apr. 12, 1991 now U.S. Pat. No. 5,243,039. As used herein, the terms meso-diaminopimelate decarboxylase, diaminopimelate decarboxylase and DAP decarboxylase are interchangeable.

As used herein, with respect to an enzyme or a subunit thereof, the term "corresponding to DAP decarboxylase" is intended to mean that the enzyme or the subunit referred to exhibits substantial sequence homology to DAP decarboxylase derived from MGA3 (e.g., $\geq 85$–$90\%$) and that the enzyme also exhibits a substantially equivalent profile of bioactivity, e.g., exhibits $\geq 85$–$90\%$ of the lysine sensitivity exhibited by DAP decarboxylase from MGA3.

As used herein, with respect to a DNA sequence which encodes DAP decarboxylase or a subunit thereof, the term "substantially pure" means that the DNA sequence is free of other DNA sequences that occur naturally in MGA3, e.g., that it has been isolated from MGA3, via the methodologies of recombinant DNA technology, as described herein, or has been prepared by known techniques of organic synthesis. Likewise, as used with respect to a DAP decarboxylase enzyme or a subunit thereof, the term "substantially pure" means that the enzyme is free of the other components of naturally occurring Bacillus, in that it has been isolated from a biological medium or has been prepared by known techniques of organic synthesis or of recombinant DNA technology.

All the patents, patent documents and publications cited herein are incorporated by reference herein.

BRIEF DESCRIPTION OF THE DRAWINGS

FIG. 3 depicts the DNA sequence of the MGA3 DAP decarboxylase gene and the amino acid sequence of the DAP decarboxylase dimer subunit.

DETAILED DESCRIPTION OF THE INVENTION

Figure 1:
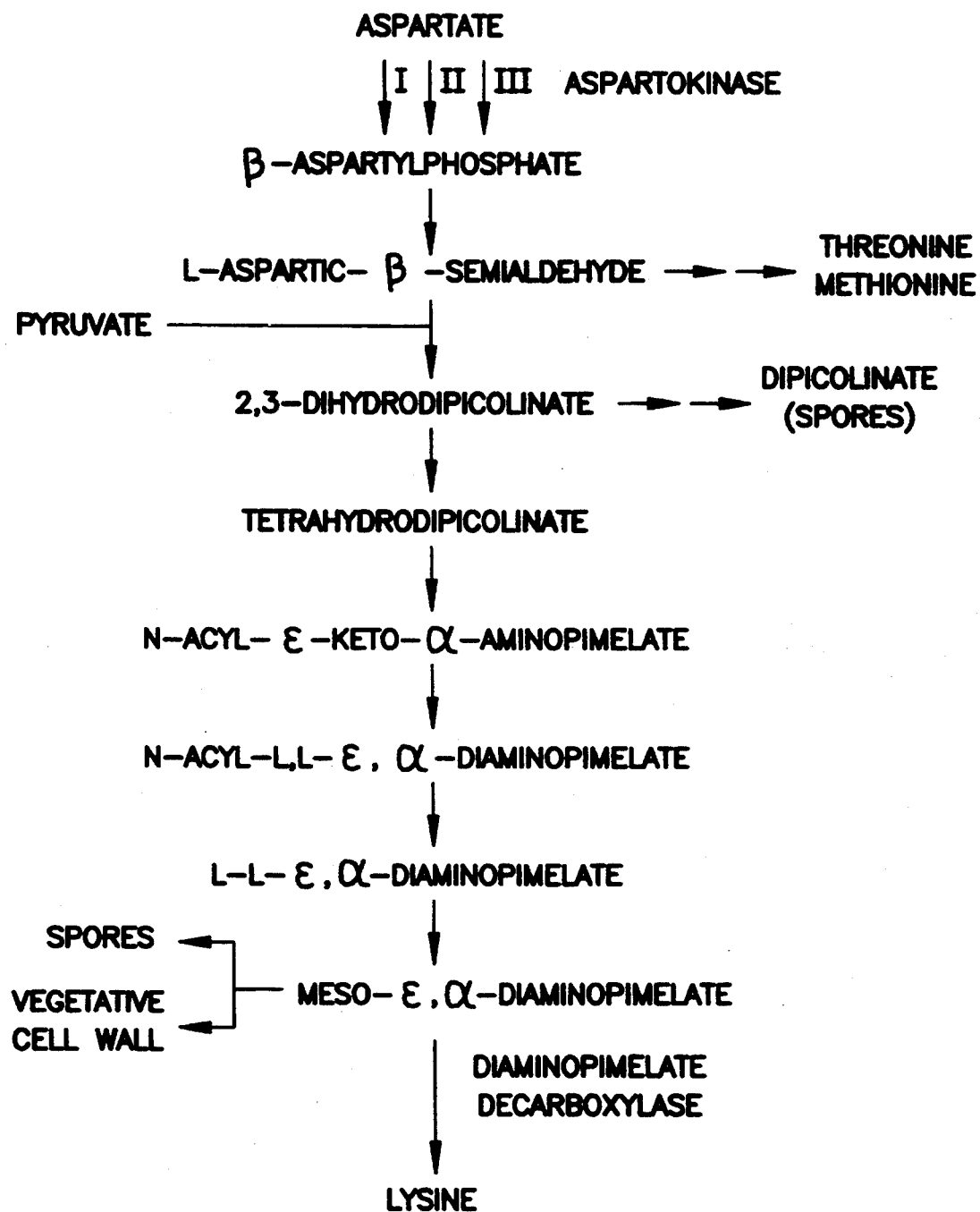
FIG. 1 is a schematic depiction of the lysine biosynthetic pathway used by Bacillus.

In bacteria, the subunit molecular weights (MW) of DAP decarboxylases from *Escherichia coli*, *Corynebacterium glutamicum*, *Pseudomonas aeruginosa* and *Brevibacterium lactofermentum* are all about 50,000, while the native molecular weights differ. A number of gram-positive DAP decarboxylases were each found to have a native MW in the range of 80,000–100,000, indicating a dimeric protein. The same relationship between the DAP decarboxylase subunit and native MGA3 DAP decarboxylase was found in the present investigation. In *E. coli*, a gram-negative bacteria, DAP decarboxylase has a native MW of 200,000, suggesting a tetrameric MW of 191,000 and a subunit MW of around 50,000.

The current model of DAP decarboxylase regulation in *E. coli* involves two genes, lysA, the gene-encoding DAP decarboxylase and lysR, an activatory regulator of the lysA gene. The two genes are transcribed divergently, separated by 121 base-pairs. P. J. White et al., *Biochem. J.*, 96, 75 (1965), determined that the molecular weight of native *E. coli* DAP decarboxylase is around 200,000. The lysA gene encodes a 420 amino acid long peptide with a predicted molecular weight of 46,099. This subunit molecular weight indicated a tetrameric native form. The lysR gene encodes a 311 amino acid polypeptide.

The synthesis of DAP decarboxylase in *E. coli* is repressed by lysine through a combined effect of lysine and the lysA product in an autogenous repression. By analysis of both the *E. coli* and the *Pseudomonas aerugenosa* lysA genes in an *E. coli* host containing a chromosomal lysA-lacZ fusion, C. F. Martin et al., *FEMS Micro. Lett.*, 36, 105 (1986) demonstrated that similar intracellular levels of either *P. aerugenosa* or *E. coli* DAP decarboxylase activity had very different effects on the expression of the *E. coli* lysA-lacZ fusion. This indicated that the lysA product itself, not its DAP decarboxylase activity, is involved in the autogenous regulation. Lysine was found to also be an effector in repression, yet this effect was only observed in the presence of sufficient intracellular DAP decarboxylase (measured by its activity).

Due to the lack of analogous genetic techniques available for gram-positive bacteria such as MGA3, analysis of the regulation of DAP decarboxylase expression is less well defined than in *E. coli*. As discussed previously, the lysine biosynthetic pathway in spore-forming bacteria is governed by two goals, the production of lysine and meso-DAP during vegetative growth and that of dipicolinic acid and meso-DAP during spore formation.

A. Rosner, in *J. Bacteriol.*, 121, 20 (1975) proposed a sequential-feedback-inhibition mechanism for controlling the cell requirements for meso-DAP during sporulation. By this postulate, lysine is accumulated at a latter stage of growth prior to spoulation. This inhibits DAP decarboxylase which, in turn, increases the intracellular level of meso-DAP necessary to fulfill the increased demand of meso-DAP into cell-wall peptidoglycan. When the biosynthesis of the spore cortex has progressed to a stage where high concentrations of meso-DAP are no longer needed, the meso-DAP concentration increases to a level sufficient to inhibit aspartokinase I, the first enzyme in the pathway, thereby decreasing the carbon flow leading to the synthesis of the aspartate family of amino acids.

Figure 2:
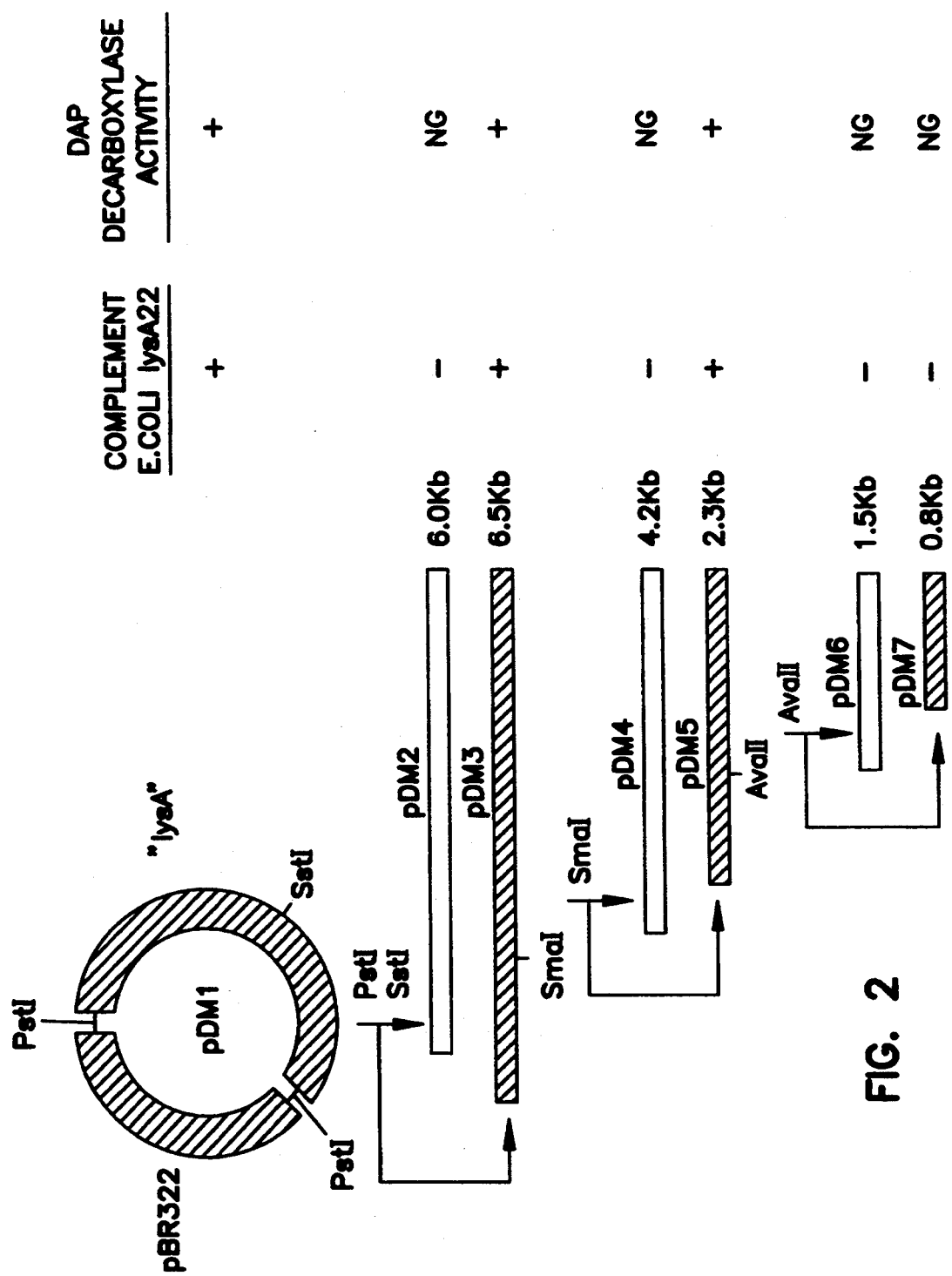
FIG. 2 schematically depicts the cloning and sequencing of the DAP decarboxylase gene.

The MGA3 lysA gene coding for diaminopimelate (DAP) decarboxylase was cloned by complementation of *E. coli* auxotrophs with a genomic library from MGA3 constructed by cloning into the PstI site of pBR322. A 12.5 Kb fragment complemented the *E. coli* DAP decarboxylase mutation. Subcloning into pUC vectors of the 12.5 Kb fragment resulted in a 2.3 Kb fragment that coded for DAP decarboxylase activity (FIG. 2). The fragment was sequenced using the Sanger dideoxy method. FIG. 3 shows the nucleotide sequence of the fragment along with the translated DAP-decarboxylase subunit amino acid sequence. A large open reading frame (ORF) was found in the DNA sequence. An ORF coding for a 432 amino acid peptide was found for DAP decarboxylase. The predicted subunit MW of 48,233 for DAP decarboxylase is in good agreement with the *B. subtilis* enzyme which has a native MW of 100,000, since DAP decarboxylase has been shown to be a dimer in *E. coli*, *Pseudomonas aeruginosa*, and *Corynebacterium glutamicum*.

The proposed start site of each protein is shown in bold in FIG. 3, and the proposed ribosome-binding site (RBS) is underlined. While no (consensus) GAGG ribosome-binding site sequence could be found for the ribosome-binding site, the underlined sequence matched the proposed ribosome-binding site in the AK II gene. It also contained possible rho-independent terminators (underlined) at the 5' end of the coding region.

The invention will be further described by reference to the following detailed Example.

EXAMPLE 1

Cloning and Sequencing of DAP Decarboxylase

1. Strains, Plasmids and Media

The *E. coli* K12 strain AT2452 thi-1 lysA22 relA1 1-, spoT1 ("lysA22") was isolated and characterized by A. I. Bukhari et al., *J. Bacteriol.*, 105, 844 (1971). *E. coli*.D-H5αF' F'/endA1 hsdR17 ($r_K^- m_K^-$) supE44 thi-1 recA-1 gyrA (Nal$^r$) relA1 D(lacZYA-argF) U169 (j80 lacZDM15) was purchased from Bethesda Research Laboratories (Gaithersburg, Md.). Bacillus MGA3 (ATCC 53907) was isolated at the Gray Freshwater Institute, Minnetonka, Minn., and described by Schendel et al, cited above.

*E. coli* were grown in the following: TB ("terrific broth" containing 1.2% tryptone, 2.4% yeast extract, 0.4% glycerol, 17 mM KH$_2$PO$_4$ and 72 mM K$_2$HPO$_4$), SOC (2% tryptone, 0.5% yeast extract, 10 mM NaCl, 2.5 mM KCl, 10 mM MgCl$_2$, 10 mM Mg$_2$SO$_4$, 20 mM glucose) (D. Hanahan, *DNA Cloning, A Practical Approach*, Vol. 1, D. M. Glover, ed., IRL Press, Oxford (1984) at pages 109–135) or M9 minimal media (T. E. Maniatis et al., *Molecular Cloning: A Laboratory Manual*, Cold Spring Harbor Lab., N.Y. (1982)) supplemented with 2.5 μg/ml of thiamine, 1.1M glucose, and 50 μg/ml of L-lysine.

2. Bacillus MGA3 were grown in minimal salts media (MS) containing the following, in one liter of distilled water: K$_2$HPO$_4$, 3.8 g; NaH$_2$PO$_4$.H$_2$O, 2.8 g; (NH$_4$)$_2$SO$_2$, 3.6 g; MgSO$_4$.7H$_2$O, 0.5 g; FeSO$_4$.7H$_2$O, 2 mg; CuSO$_4$.5H$_2$O, 40 μg; H$_3$BO$_3$, 30 μg; MnSO$_4$.H$_2$O, 200 μg; ZnSO$_4$.7H$_2$O, 200 μg; Na$_2$MoO$_4$.2H$_2$O, 47 μg; CaCl$_2$.H$_2$O, 5.3 mg; CaCl$_2$.6H$_2$O, 40 μg. The pH was adjusted to 7.4 prior to autoclaving. The minimal vitamin (MV) medium was the MS medium supplemented with biotin, 50 μg/liter, and vitamin B$_{12}$, 1 μg/liter. Yeast extract (MY) medium was MV medium containing 0.5 g/liter yeast extract. Both MV and MY media contained 0.5% (vol/vol) methanol. MV or MY plating media contained 1.5% bacto-agar and the following modifications: (NH$_4$)$_2$SO$_2$ was reduced to 1.3 g/liter, K$_2$HPO$_4$ to 0.4 g/liter and NaH$_2$PO$_4$.H$_2$O was omitted.

The *E. coli* plasmid pUC18 (ampicillin$^R$) was a gift from Dr. P. B. Hackett and the plasmid pUC19 (chloramphenicol$^R$) was a gift of Dr. J. Fuchs.

3. Biochemicals

Restriction endonucleases, T4 DNA ligase, Klenow fragment of DNA polymerase 1, and Bacterial Alkaline Phosphatase were purchased from Bethesda Research Laboratories (Gaithersburg, Md.). Sequenase, dideoxynucleotide mixes, and Universal (-20) and -40 forward-sequencing primer were purchased from U.S. Biochemical Corp. (Cleveland, Ohio). The T7 reverse sequencing primer, exonuclease 111/S1 nuclease "Erase-a-Base" nested deletion kit was purchased from Promega Corp. (Madison, Wis.). $\alpha^{32}$P-dATP (1000 Ci/mmol) was purchased from Amersham Corp. (Arlington Heights, Ill.). $\alpha^{32}$P-dCTP (3000 Ci/mmol) and $\gamma^{32}$P-dATP (3000 Ci/mmol) were purchased from Dupont-NEN (Boston, Mass.).

1,7-$^{14}$C-diaminopimelate (mixed isomers, 29 mCi/mmol) was purchased from ICN Biochemicals (Irvine, Calif.). Hyamine hydroxide, β-mercaptoethanol, L-lysine, and other basic reagents were purchased from Sigma Chemical Co. (St. Louis, Mo.).

4. Plasmid Mini-Preps

Plasmid DNA from *E. coli* was isolated by the method of H. C. Birnham et al., *Nucl. Acids Res.*, 7, 1513 (1979), with the following modifications. One ml of cells from an overnight TB culture was pelleted in a 1.5 ml microfuge tube and resuspended in 100 μl of solution A (50 mM glucose, 25 mM Tris-HCl, pH 8.0, 10 mM EDTA). To this mixture 200 μl of solution B (0.2N NaOH, 1% SDS) was added, followed by inversion several times to ensure mixing. 175 μl of solution C (3M sodium acetate, pH 4.8) was then added, the eppendorf tube mixed by inversion, and placed at −20° C. for 20 minutes. The solution was pelleted for 5 minutes in an eppendorf centrifuge and the supernatant saved. The DNA in the supernatant solution was then precipitated with 400 μl of isopropanol, resuspended in 200 μl of 03M NaCl and precipitated again with 400 μl of 95% ethanol. The pellet was then air-dried and resuspended in 50 μl TE (10 mM Tris-HCl, pH 8.0, 1 mM EDTA). For a typical restriction analysis, 5 μl of this solution was used with 1 μl of 10 μg/ml RNAse, and the restriction enzyme of choice.

5. Plasmid Midi-Preps

Purification of plasmid for double-stranded dideoxy-chain termination sequencing was performed according to the procedure of P. Kreig et al. (Promega Catalog, Madison, Wis. (1986)). Fifty ml of overnight culture was pelleted in a 30 ml corex tube at 5000 rpm in a Beckmann JA10 rotor. The pellet was resuspended in 6 ml of 25 mM Tris-HCl, pH 8.0, 10 mM EDTA, 15% sucrose, and 2 mg/ml lysozyme (added fresh) and incubated on ice for 20 minutes. To this solution was added 20 ml of 0.2N NaOH, 1% SDS. The mixture was inverted gently and incubated on ice for 10 minutes. 7.5 ml of 3M sodium acetate, pH 4.8, was added and the solution again mixed gently by inversion. The mixture was centrifuged in a Beckmann JA10 rotor at 15000 rpm for 15 minutes. The supernate was removed and the nucleic acids precipitated with 0.6 volume of isopropanol. The resulting pellet was then resuspended in 5 ml of TE containing 50 μg/ml RNAse. After incubation at 37° C. for 20 minutes, the solution was extracted twice with 5 ml of phenol saturated with TE, and once with 5 ml of phenol:chloroform (1:1). The plasmid DNA was then pelleted with 2.5 volumes of 95% ethanol. The resulting pellet was resuspended in 1.6 ml of H$_2$O to which 0.4 ml of 4M NaCl was added and the solution mixed. Two ml of 13% polyethylene-glycol (MW-8000) was then added and the mixture incubated on ice for 1 hour. The mixture was then centrifuged at 10,000 rmp (Beckmann JA20) and the pellet washed with 70% and then 95% ethanol. Finally the pellet was dissolved in 200 μl of TE and the plasmid concentration determined by optical density at A260.

6. Preparation of Bacillus MGA3 Chromosomal DNA

Chromosomal DNA was isolated by the procedure of R. E. Yasbin et., *J. Bacteriol.*, 121, 296 (1975), with the following modifications. Bacterial cells were incubated overnight in 100 ml of MY media (Bacillus MGA3) at 50° C. and centrifuged 4000×g in a Beckman JA20 rotor for 10 min. The cell pellet was resuspended in 0.05× of the starting volume in STET buffer (5% Sucrose, 8% Triton-X 100, 50 mM EDTA, 50 mM Tris-Cl, pH 8.0) plus lysozyme (100 μl/ml final concentration; Sigma) for 1 hour at 37° C. Proteinase K (40 μl/ml final concentration) and RNase A (20 μg/ml final conc.) were added and the preparation allowed to incubate a further hour at 37° C. Sodium dodecyl sulfate (SDS) and Sarkosyl (0.1 ml from a stock solution containing 10% SDS and 8% Sarkosyl per 5 ml DNA preparation) were added and gently mixed at 50° C. until all membrane material was dissolved (around 20 minutes). The preparation was then extracted twice with TE saturated phenol and once with chloroform (24:1, chloroform: isoamyl alcohol). DNA was then isolated by layering onto the preparation 2 volumes of ice-cold 95% ethanol and spooling the DNA around a glass rod. The DNA remaining on the glass rod was washed twice with 95% ethanol, air dried 10 minutes at room temperature and redissolved in TE (10 mM Tris-Cl pH 8.0, 1 mM EDTA).

7. DNA Cloning Experiments

All restriction enzymes, T4 ligase, Klenow fragment, and Bacterial Alkaline Phosphatase, were used as recommended by the suppliers. DNA fragments were analyzed by horizontal electrophoresis in agarose gels with TAE buffer. Lamda DNA (BRL) cut with Hind 111 and Bst E 11 was used as a molecular weight standard as well as a concentration reference. DNA fragments were isolated from low melting point agarose (BioRad) by the method of Langridge et al., *Anal. Biochem.*, 103, 264 (1980).

8. Transformation of *E. coli*, $CaCl_2$-RbCl Transformation

Transformation of *E. coli* was performed essentially as described in Hanahan, cited above. *E. coli* cells were grown in 500 ml of SOC media in a 2l shake flask to a cell density of $4$–$7 \times 10^7$ CFU/ml (O.D. of 1.0). The cells were centrifuged at $4000 \times g$ for 10 minutes and resuspended in 167 ml (⅓ volume) of sterile RF1 (100 mM RbCl, 50 mM $MgCl_2.4H_2O$, 30 mM potassium acetate, 10 mM $CaCl_2.2H_2O$, 15% glycerol—adjusting pH to 5.8 with 0.2M acetate acid). The cells were then incubated on ice for 20 minutes and centrifuged at $4000 \times g$ for 10 minutes. This final pellet resuspended in 42 ml (1/12 volume) sterile RF2 (10 mM, pH 6.8, 10 mM RbCl, 75 mM $CaCl_2 2H_2O$, 15% glycerol) and incubated on ice for 15 minutes. The competent cells were distributed into 200 µl aliquots and quick frozen in a dry ice/ethanol bath and placed at $-70°$ C.

For a simple transformation a tube(s) was removed and allowed to thaw at room temperature. The DNA was added in a volume of less than 20 µl, mixed by swirling the tube, and incubated on ice for 30 minutes. The cells were then heat shocked at 42° C. for one minute and immediately placed on ice. 800 µl of SOC medium was then added and the cells incubated at 37° C. for 30 minutes. Finally, the cells were plated on the appropriate media for selection.

9. Transformation of *E. coli*, Electroporation

The *E. coli* cells were grown in 500 ml of TB to an optical density of ($OD_{600nm}$) of 1.0. The cells were harvested by centrifugation $4000 \times g$ for 15 minutes. The cell pellet was then washed twice in 500 ml of sterile $H_2O$ and resuspended in 10 ml of cold 10% glycerol. The cells were then distributed in 50 µl aliquots, quick frozen in a dry ice/ethanol bath and stored at $-70°$ C.

Transformation was performed by mixing 1 µl of DNA solution (10 ng-10 ug/µl) with the 50 µl electrocompetent cells, placing the solution inside an electrode (BTX), and pulsing with 17 Kv/cm for 5 ms. The transformed cells were then immediately placed in 300 µl of SOC medium and incubated at 37° C. for 30 minutes. Finally the cells were plated on the appropriate media for selection.

10. DNA Sequencing

The pUC18am-lys2.3 Sma1-Sst1 fragment was sequenced by the dideoxynucleotide chain termination method of F. Sanger et al. (*PNAS USA*, 71, 5463 (1977)), using M13 universal primers (-20 and -40) (New England BioLab) in the forward direction and the T7 reverse sequencing primer (Promega) for the reverse direction. Gaps in the complete sequence were filled in by synthezing primers on an Applied Biosystems primer system according to the manufacturer's recommendations. Sequencing reactions were separated using buffer gradient urea/acrylamide gels as described by M. D. Biggin et al. (*PNAS USA*, 80, 3963 (1983)). Sequence data was analyzed using Intellegenetics software.

11. Preparation of Cell Extracts

*E. coli* lysA22 cells were grown to an $OD_{600nm}$ of between 0.7 and 1.0 in 100 ml of minimal M9 media supplemente with 50 µl/ml L-lysine (for those plasmids not encoding a DAP decarboxylase activity) and appropriate antibiotic. The cells were washed in 10 ml of DAP decarboxylase enzymatic assay buffer (see below), collected and resuspended in 3 ml of the same buffer, and sonicated on ice for 30 seconds at 95% using a Biotip sonicator. The cell debris was then centrifuged at $16000 \times g$ for 20 minutes and the cell supernatant removed and assayed for protein concentration and DAP decarboxylase activity 12. Measurement of DAP Decarboxylase Activity DAP decarboxylase assays were performed on column fractions or crude *E. coli* cell extracts as described by J. G. Kelland et al., *Biochemistry*, 24, 3263 (1985), with the following modifications. The assay mixtures contained 50 mM potassium phosphate and 50 mM MOPS buffers at pH 7.5, 1 mM EDTA, 1 mM β-mercaptoethanol, 0.2 µl pyridoxal-5'-phosphate, 10 nCi of [1,7-$^{14}$C] diaminopimelate (mixed isomers) and enzyme to a final volume of 1 ml. The reaction was performed in scintillation vials with caps containing a 1.5 cm × 1.5 cm piece of Whatmann 3MM filter paper saturated with 20 µl of 1M hyamine hydroxide as a $^{14}CO_2$ trapping agent. The reaction was initiated by addition of enzyme and the assay mixture incubated at 50° C. for 5 minutes with continual shaking. The reaction was quenched by addition of 200 µl of 10% TCA and the vial shaken in additional 15 minutes to ensure complete $^{14}CO_2$ evolution. The filter paper was then removed and counted in 10 ml of EcoScint scintillation cocktail on a Beckman LS7000 scintillation counter. One unit of DAP decarboxylase activity is defined as the amount of enzyme which liberates 1 umol of $CO_2$ per minute. Protein concentrations were determined by the absorbance at 280 nm or by a modified Lowry method (*J. Biol. Chem.*, 193, 265 (1951)).

13. Results and Discussion

A. Subcloning of an *E. coli* Strain AT2452 (lysA22)

The plasmid PDM1 shown in FIG. 2 carries a 12.5 Kb Pst1 fragment isolated from Bacillus MGA3 chromosomal DNA in the Pst1 site on the plasmid pBR322. This fragment and restriction fragments thereof, were subcloned into pUC19cm vectors and used to complement *E. coli* strain AT2452 (lysA22). This allowed the localization of the Bacillus MGA3 lysA-complementing gene within a 2.3 Kb Sma1-Sst1 fragment. Further restriction analysis indicated neither Ava11-Sst1 fragment nor the Sma1-Ava11 was able to complement the *E. coli* lysA22 auxotroph indicating the Bacillus MGA3 meso-DAP decarboxylase encoding fragment lies completely within the Sma1-Sst1 fragment.

B. Nucleotide Sequence of the lysA-complementing Gene

The nucleotide sequence of the 2.3 Kb Sma1-Sst1 fragment was determined by the method of F. Sanger et al., *PNAS USA*, 71, 5463 (1977). Deletion subclones of the Sma1-Sst1 fragment were created utilizing the Erase-A-Base kit (Promega Corp.) as recommended by the manufacturer. Subclones were sequenced using "universal" -20 and -40 primers and the T7 reverse sequencing primer with gaps in the sequence filled by primers synthesized at BPTI. The strategy allowed complete determination of both strands. As shown in FIG. 3, there is one large open reading frame with an initiating ATG codon and a putative ribosome-binding site (RBS) GGGA six bases upstream of the initiating methionine codon. The open reading frame encodes a 437 amino acid peptide corresponding to a 48,223 kD protein. This is the DAP decarboxylase dimer subunit.

One hundred and seventy-four basepairs upstream from the translation start site is a putative promoter structure, -10/-35 region closely matching the promoter identified in the aspartokinase II gene. Immediately downstream of the Bacillus MGA3 meso-DAP decarboxylase open reading frame is a region of dyad symmetry. followed by a string of pyrimidine bases indicative of a ρ-independent termination site in other bacteria.

Analysis of the Bacillus MGA3 lysA 3' flanking sequences reveal another open reading frame 387 basepairs downstream of the lysA stop codon. The open reading frame encodes a 102 amino acid peptide and possesses a typical ribosome-binding site concensus ("GAGG") immediately upstream of the initiating methionine codon. The identity of this putative open reading frame has yet to be determined.

C. DAP Decarboxylase Purification

For all of the following physical and kinetic analysis, the Bacillus MGA3 meso-DAP decarboxylase was purified from an *E. coli* lysA22 auxotrophic mutant containing the pDM5 plasmid. The purification occurred as per Y. Asada et al., *Biol. Chem.*, 45, 1513 (1981), with the following modifications. All steps of the purification occurred at 4° C. *E. coli* AT2452 thi 1 lysA22 relA11-spoT1:pDM1 containing the recombinant Bacillus MGA3 lysA gene was grown in a 30 liter New Brunswick fermentor with base addition using TB media as described in materials and methods.

For a typical purification, 65 grams of wet cell paste was resuspended in 200 ml of 4° C. purification buffer #1 (50 mM $KPO_4$, pH 7.5, 1 mM EDTA, 20 μM PLP, 0.01% 2-mercaptoethanol) and disrupted by passage twice through a French Press. The supernatant obtained by centrifugation for 1 hour at 20,000 rpm in a Beckmann JA20 rotor at 4° C., was fractionated with ammonium sulfate (25% to 40% saturation). The resulting fraction was desalted by passage through a Sephadex G-25 column (27 cm×2.5 cm) and the protein peak diluted two-fold with purification buffer #1 before application to a DEAE-agarose column equilibrated with the same buffer.

After washing the column, the enzyme was eluted with a potassium chloride gradient (0 to 300 mM KCl) in purification buffer #1. Active fractions, eluting around 200 mM KCl, were pooled and dialyzed against purification buffer #2 (10 mM $KPO_4$, pH 6.5, 1 mM EDTA, 20 μM PLP, 0.01% 2-mercaptoethanol). The enzyme pool was then applied to a hydroxyapatite column (20 cm×1 cm) previously equilibrated in purification buffer #2 and further washed in purification buffer #2. The enzyme was eluted with a potassium phosphate gradient (10 mM to 300 mM $KPO_4$) in purification buffer #2 with the active fractions centering around 60 mM $KPO_4$. The enzyme was then pooled and dialyzed against purification buffer #1 prior to: 1) application to Sephacryl S-300 sizing column, 2) kinetic analysis, 3) further purification on a FPLC mono-Q column prior to N-terminal sequencing.

D. DAP Decarboxylase Enzyme—Physical Characterizations

1. Molecular Weight Analysis

As determined by SDS-PAGE analysis, the subunit molecular weight of DAP decarboxylase is around 50,000. This correlates well with the predicted molecular weight of the Bacillus MGA3 DAP decarboxylase dimer subunit sequence (48,223 MW). The native molecular weight is 86,000 as determined by the Sephacryl S-300 gel filtration method of P. Andews, *Biochem. J.*, 91, 222 (1965).

2. N-Terminal Sequencing

Prior to N-terminal sequencing, hydroxyapatite fractions were pooled and concentrated via ultrafiltration and applied to a FPLC mono-Q column previously equilibrated with purification buffer #1. Using a potassium chloride gradient (1 to 1M KCl) in purification buffer #1, DAP decarboxylase-active fractions were eluted at around 100 mM KCl. These fractions were pooled and protein was TCA-precipitated prior to SDS-polyacrylamide gel electrophoresis and subsequent transfer to a ProBlott membrane (BioRad). Electrophoretic transfer of protein of the ProBlott polyvinylidene diflouride (PVDF) membrane was performed as described by P. Matsudaira, *J. Biol. Chem.*, 262, 10035 (1987). The DAP decarboxylase protein bands, identified by relative mobility compared to previous SDS-PAGE gels, were excised and stored in glass vials. N-terminal sequence analysis was performed at the University of Minnesota, Microchemical facility.

The N-terminal sequence determined, Met-Tyr-Phe-X-X-Thr-X-Lys-Val, matches the predicted start site as exactly indicated from the DNA sequence shown in FIG. 3.

3. DAP Decarboxylase Enzyme—Kinetic Characterizations

For Bacillus MGA3 meso-DAP decarboxylase, the concentration of diaminopimelate necessary for half-maximal activity was determined to be 0.80 mM. L-lysine behaved as a competitive inhibitor (Ki=0.93 mM) with respect to diaminopimelate. Other amino acids alone or in combination with lysine did not inhibit the enzyme (Table 1).

TABLE 1.

| Amino Acid Addition (5 mM) | Enzyme Inhibition at 37° C. % Inhibition | |
|---|---|---|
| | DAP Decarboxylase | Aspartokinase II |
| none | 0 | 0 |
| lys | 85 | 96 |
| thr | 10 | 0 |
| met | 19 | 8 |
| ile | 16 | 0 |
| lys (0.5 mM) | 41 | 76 |
| lys (0.5 mM), thr (5 mM) | 37 | 77 |

What is claimed is:

1. An isolated DNA molecule from methylotrophic, thermotolerant *Bacillus sp.* MGA3, which encodes a polypeptide corresponding to SEQ ID NO:2, wherein the polypeptide of SEQ ID NO:2 is the αβ dimer subunit of lysine-sensitive diaminopimelate decarboxylase of the methylotrophic, thermotolerant *Bacillus sp.* MGA3.

2. An isolated DNA molecule according to claim 1, having the sequence of SEQ ID NO:1.

* * * * *

UNITED STATES PATENT AND TRADEMARK OFFICE
CERTIFICATE OF CORRECTION

PATENT NO.  : 5,426,052

DATED       : June 20, 1995

INVENTOR(S) : Michael C. Flickinger et al.

It is certified that error appears in the above-identified patent and that said Letters Patent is hereby corrected as shown below:

On the Title page, before the section "CROSS REFERENCE TO RELATED APPLICATION", insert the following:

--GOVERNMENT SUPPORT
This invention was made with government support under grant number DE-AC02-82ER12029 by the U.S. Department of Energy. The Government has certain rights in the invention.--

At column 3, line 18, for "FIG. 3" read --FIGS. 3A-3D--

At column 5, line 14, for "$_{30}$ µg" read --30 µg--

At Column 10, in Table 1, line 11, should read --lys(0.5mM),thr (5mM)--.

Signed and Sealed this

Ninth Day of July, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2368 base pairs (B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: DAP Decarboxylase Gene (ix) FEATURE:
(A) NAME/KEY: CDS
(B) LOCATION: 265..1560

(xi) SEQUENCE DESCRIPTION: SEQ ID NO:1:

```
CGGGTCAAAA ATACGCCCAA GCATCATTCA TACAAAAAAT CGATACCGCC AACCGACATA      60

AGAAAAGCAG AAGCATTATG CAACTTGAAT CAATTGCGAA TTTTCAAATC TTATGGTAAG     120

TTTGTTTTTA TTAAAGAATC CATTAAGGGG CAGAAATCAA TACCTACTTG AAAGATTCTA     180

TTCATTTGTT TATATTCAAA ATAATTCATT TTTAATAAAT ATTCGGGATC GACATATTGA     240

GTGATAAGGG GAATGGGAAC AGAA ATG TAT TTT CAT GGC ACA ACA AAG GTA        291
                           Met Tyr Phe His Gly Thr Thr Lys Val
                             1               5

AAT GAA AAG GGA CAT TTA GAA ATC GGC GGA GTG GAT ACG ATC GAA CTT       339
Asn Glu Lys Gly His Leu Glu Ile Gly Gly Val Asp Thr Ile Glu Leu
 10              15                  20                  25

GCA CAA AAG TAT GGC ACG CCT CTA TAT GTA TAC GAC GTT GCT TTA ATT       387
Ala Gln Lys Tyr Gly Thr Pro Leu Tyr Val Tyr Asp Val Ala Leu Ile
             30                  35                  40

CGC GAG CGG GCT AGA GGG TTT AAA AAT ACG TTT GAT GAG CTT GGT ATT       435
Arg Glu Arg Ala Arg Gly Phe Lys Asn Thr Phe Asp Glu Leu Gly Ile
         45                  50                  55

AAA GCT CAA GTT GCA TAT GCA AGC AAA GCA TTT TCT ACA GTA GCA ATG       483
Lys Ala Gln Val Ala Tyr Ala Ser Lys Ala Phe Ser Thr Val Ala Met
     60                  65                  70

ATT CAG CTT GCA GAA GAG GAA GGC TTG TCA CTG GAT GTT GTA TCA GGC       531
Ile Gln Leu Ala Glu Glu Glu Gly Leu Ser Leu Asp Val Val Ser Gly
 75                  80                  85

GGA GAG CTT TAT ACA GCT TTG GTC GCA GGT TTC CCT GTT CAT AAA ATC       579
Gly Glu Leu Tyr Thr Ala Leu Val Ala Gly Phe Pro Val His Lys Ile
 90                  95                 100                 105

CAT TTT CAT GGT AAT AAT AAA AGC AGA GCC GAA CTG GAA ATG GCA TTG       627
His Phe His Gly Asn Asn Lys Ser Arg Ala Glu Leu Glu Met Ala Leu
             110                 115                 120

GAG CAC CAA ATA GGC TGC ATT GTT GTA GAT AAT TTT CAT GAA CTT GAT       675
Glu His Gln Ile Gly Cys Ile Val Val Asp Asn Phe His Glu Leu Asp
         125                 130                 135

CTT ATT GAT TCC ATA TGT TCC GAA AAG AAT GTA AAA ACA AAT ATT CTT       723
Leu Ile Asp Ser Ile Cys Ser Glu Lys Asn Val Lys Thr Asn Ile Leu
     140                 145                 150

TTG AGA GTA ACT CCA GGA ATT GAG GCT CAT ACG CAT GAC TAT ATT TTA       771
Leu Arg Val Thr Pro Gly Ile Glu Ala His Thr His Asp Tyr Ile Leu
 155                 160                 165

ACG GGG CAG GAA GAC TCT AAG TTT GGG TTT GAC CTT CAA AAC GGC CAG       819
Thr Gly Gln Glu Asp Ser Lys Phe Gly Phe Asp Leu Gln Asn Gly Gln
 170                 175                 180                 185

GCT GAA AAA GCA CTT CAA ATT GCG TTA AAT TCA AAC TTT GTT GAA GTT       867
Ala Glu Lys Ala Leu Gln Ile Ala Leu Asn Ser Asn Phe Val Glu Val
             190                 195                 200

CTC GGG GTT CAC TGC CAT ATT GGT TCA CAA ATT TTT GAT ACT ACC GGA       915
Leu Gly Val His Cys His Ile Gly Ser Gln Ile Phe Asp Thr Thr Gly
             205                 210                 215

TTT GTT CTA GCA GCA AGA AAA ATC TTT GAA AAA TTA AAG GAA TGG AAA       963
Phe Val Leu Ala Ala Arg Lys Ile Phe Glu Lys Leu Lys Glu Trp Lys
             220                 225                 230
```

| | | | | | | | | | | | | | | | | |
|---|---|---|---|---|---|---|---|---|---|---|---|---|---|---|---|---|
| GAT | AGG | CTG | TCA | TAC | GAG | CCA | AAA | GTA | TTA | AAT | CTT | GGA | GGC | GGA | TTC | 1011 |
| Asp | Arg | Leu | Ser | Tyr | Glu | Pro | Lys | Val | Leu | Asn | Leu | Gly | Gly | Gly | Phe | |
| | 235 | | | | 240 | | | | | 245 | | | | | | |
| GGA | ATT | CGT | TAT | ACA | GAG | GAA | GAT | GAT | CCT | ATT | CCA | GCA | TCT | CAA | TAT | 1059 |
| Gly | Ile | Arg | Tyr | Thr | Glu | Glu | Asp | Asp | Pro | Ile | Pro | Ala | Ser | Gln | Tyr | |
| 250 | | | | | 255 | | | | | 260 | | | | | 265 | |
| GTG | AAA | GAA | ATT | ATT | AAC | GAA | GTG | AAA | AAA | CAA | GTA | TCC | GCT | TAT | TCC | 1107 |
| Val | Lys | Glu | Ile | Ile | Asn | Glu | Val | Lys | Lys | Gln | Val | Ser | Ala | Tyr | Ser | |
| | | | | 270 | | | | | 275 | | | | | 280 | | |
| ATG | AAA | ATG | CCT | GAA | ATT | TGG | ATT | GAA | CCT | GGG | CGT | TCT | CTT | GTT | GGT | 1155 |
| Met | Lys | Met | Pro | Glu | Ile | Trp | Ile | Glu | Pro | Gly | Arg | Ser | Leu | Val | Gly | |
| | | | 285 | | | | | 290 | | | | | 295 | | | |
| GAT | GCT | GGA | ACA | ACA | TTA | TAT | CAG | ATC | GGT | TCT | AGG | AAA | GAT | GTC | CCA | 1203 |
| Asp | Ala | Gly | Thr | Thr | Leu | Tyr | Gln | Ile | Gly | Ser | Arg | Lys | Asp | Val | Pro | |
| | | 300 | | | | | 305 | | | | | 310 | | | | |
| AAC | GTG | AGG | CAT | TAT | GTG | GCT | GTA | GAC | GGA | GGT | ATG | AGT | GAC | AAT | ATC | 1251 |
| Asn | Val | Arg | His | Tyr | Val | Ala | Val | Asp | Gly | Gly | Met | Ser | Asp | Asn | Ile | |
| | 315 | | | | | 320 | | | | | 325 | | | | | |
| CGC | CCC | GCT | TTG | TAC | AAT | GCT | AAG | TAT | GAA | GCT | GTA | TTG | GCA | AAT | AAA | 1299 |
| Arg | Pro | Ala | Leu | Tyr | Asn | Ala | Lys | Tyr | Glu | Ala | Val | Leu | Ala | Asn | Lys | |
| 330 | | | | | 335 | | | | | 340 | | | | | 345 | |
| CCA | CTT | GCG | AAA | GCG | GAT | GAA | ACA | GTT | TCA | ATT | GCA | GGC | AAG | TGC | TGT | 1347 |
| Pro | Leu | Ala | Lys | Ala | Asp | Glu | Thr | Val | Ser | Ile | Ala | Gly | Lys | Cys | Cys | |
| | | | | 350 | | | | | 355 | | | | | 360 | | |
| GAA | TCA | GGA | GAT | ATG | CTT | ATA | TGG | GAT | TTG | CCT | CTT | CCT | AAA | GCG | GAC | 1395 |
| Glu | Ser | Gly | Asp | Met | Leu | Ile | Trp | Asp | Leu | Pro | Leu | Pro | Lys | Ala | Asp | |
| | | | 365 | | | | | 370 | | | | | 375 | | | |
| AGT | GAT | GAT | ATA | CTT | GCT | GTC | TTT | TGT | ACC | GGA | GCA | TAT | GGT | TAT | TCA | 1443 |
| Ser | Asp | Asp | Ile | Leu | Ala | Val | Phe | Cys | Thr | Gly | Ala | Tyr | Gly | Tyr | Ser | |
| | | 380 | | | | | 385 | | | | | 390 | | | | |
| ATG | GCA | AAT | AAT | TAT | AAC | CGG | ATT | CCA | AGG | CCG | GCC | GTG | GTA | TTT | GTT | 1491 |
| Met | Ala | Asn | Asn | Tyr | Asn | Arg | Ile | Pro | Arg | Pro | Ala | Val | Val | Phe | Val | |
| | 395 | | | | | 400 | | | | | 405 | | | | | |
| GAG | AAT | GGG | GAA | TCA | ATG | CTT | GTA | GTG | AAA | CGG | AAA | CAT | ATG | AGG | ACC | 1539 |
| Glu | Asn | Gly | Glu | Ser | Met | Leu | Val | Val | Lys | Arg | Lys | His | Met | Arg | Thr | |
| 410 | | | | | 415 | | | | | 420 | | | | | 425 | |
| TCG | TCC | GCA | ATG | ATC | TGC | CTT | TAAAAGAAAG | | AGTAAGATAC | | TAAGCTGCCG | | | | | 1590 |
| Ser | Ser | Ala | Met | Ile | Cys | Leu | | | | | | | | | | |
| | | | | 430 | | | | | | | | | | | | |

| | | | | | |
|---|---|---|---|---|---|
| GTTCTGGCA | GCTTAGTTAC | TAGAAGATGG | ATTAAAAATG | CATTTTAGTG | TAGAATTAGG | 1650 |
| AACAGCTTAT | TGTTTATATT | ATAGGCTGGG | AGGATCTGAT | TCATTTATGA | AAAAGAAAA | 1710 |
| TTGGTTGGTG | TTTTCTTTTA | TTCTTGTCAT | GTCGTTGCTA | TGGGGATGTT | TCTATTGGTT | 1770 |
| CTTTATTGCG | CCTATACAAT | GATATAAAAT | GACCTTGACA | AGAAATTGAA | GAATTGCCAT | 1830 |
| CATTTTTATA | TGATAAGGTC | AATTACTAGA | CACGCCATAA | CACATTTCAA | CATATACTAA | 1890 |
| ATGTCAAAGT | TCATAAATTG | GTGAACAAAA | AAGTTCGAAT | TCATTAATGA | GGGATCAGTA | 1950 |
| TGTTAATACG | TTATAAGAAA | GCATTTGAAA | AAATAGCAAT | GGGACTTTTA | TCCTTTATGC | 2010 |
| CAAATGAGAA | GGATTTGAAG | AAACTTCAGC | AAACGATGAA | GCAGTATGAA | ACCGAAGAAG | 2070 |
| ACCGACAGTT | GTTTCTGTGG | AAGGAAGAGG | AAGATATTAT | CGGCCTTATA | GGTGTACTTG | 2130 |
| TTGTTAATGA | ATACGAAGTC | GAAATACATC | ATATATCTGT | TAACCCTTCA | CATCGTCATC | 2190 |
| AAGGTATAGG | CAAGAGTATG | GTAAAGGCAT | TAAGAGATAT | TTATCCTGAT | AAAGAGCTGA | 2250 |
| TACCAAATGA | AAATACAGCG | GCTTTCATAG | AAAAATGTGA | GATTTGTCAT | GGCAGTGAAT | 2310 |
| AATGATTATT | CGCTGCCTTT | TTTCTTTCGA | TTGATCATTG | CAATTTCCGT | TCTTTATG | 2368 |

( 2 ) INFORMATION FOR SEQ ID NO:2:

( i ) SEQUENCE CHARACTERISTICS:
    ( A ) LENGTH: 432 amino acids
    ( B ) TYPE: amino acid
    ( D ) TOPOLOGY: linear ( i i ) MOLECULE TYPE: protein ( v i i ) IMMEDIATE SOURCE:
    ( B ) CLONE: Decarboxylase ( x i ) SEQUENCE DESCRIPTION: SEQ ID NO:2:

```
Met Tyr Phe His Gly Thr Thr Lys Val Asn Glu Lys Gly His Leu Glu
 1               5                  10                  15

Ile Gly Gly Val Asp Thr Ile Glu Leu Ala Gln Lys Tyr Gly Thr Pro
             20                  25                  30

Leu Tyr Val Tyr Asp Val Ala Leu Ile Arg Glu Arg Ala Arg Gly Phe
             35                  40                  45

Lys Asn Thr Phe Asp Glu Leu Gly Ile Lys Ala Gln Val Ala Tyr Ala
     50                  55                  60

Ser Lys Ala Phe Ser Thr Val Ala Met Ile Gln Leu Ala Glu Glu Glu
 65                  70                  75                  80

Gly Leu Ser Leu Asp Val Val Ser Gly Gly Glu Leu Tyr Thr Ala Leu
                 85                  90                  95

Val Ala Gly Phe Pro Val His Lys Ile His Phe His Gly Asn Asn Lys
                100                 105                 110

Ser Arg Ala Glu Leu Glu Met Ala Leu Glu His Gln Ile Gly Cys Ile
             115                 120                 125

Val Val Asp Asn Phe His Glu Leu Asp Leu Ile Asp Ser Ile Cys Ser
     130                 135                 140

Glu Lys Asn Val Lys Thr Asn Ile Leu Leu Arg Val Thr Pro Gly Ile
145                 150                 155                 160

Glu Ala His Thr His Asp Tyr Ile Leu Thr Gly Gln Glu Asp Ser Lys
                165                 170                 175

Phe Gly Phe Asp Leu Gln Asn Gly Gln Ala Glu Lys Ala Leu Gln Ile
             180                 185                 190

Ala Leu Asn Ser Asn Phe Val Glu Val Leu Gly Val His Cys His Ile
     195                 200                 205

Gly Ser Gln Ile Phe Asp Thr Thr Gly Phe Val Leu Ala Ala Arg Lys
210                 215                 220

Ile Phe Glu Lys Leu Lys Glu Trp Lys Asp Arg Leu Ser Tyr Glu Pro
225                 230                 235                 240

Lys Val Leu Asn Leu Gly Gly Gly Phe Gly Ile Arg Tyr Thr Glu Glu
                245                 250                 255

Asp Asp Pro Ile Pro Ala Ser Gln Tyr Val Lys Glu Ile Ile Asn Glu
             260                 265                 270

Val Lys Lys Gln Val Ser Ala Tyr Ser Met Lys Met Pro Glu Ile Trp
     275                 280                 285

Ile Glu Pro Gly Arg Ser Leu Val Gly Asp Ala Gly Thr Thr Leu Tyr
     290                 295                 300

Gln Ile Gly Ser Arg Lys Asp Val Pro Asn Val Arg His Tyr Val Ala
305                 310                 315                 320

Val Asp Gly Gly Met Ser Asp Asn Ile Arg Pro Ala Leu Tyr Asn Ala
                325                 330                 335

Lys Tyr Glu Ala Val Leu Ala Asn Lys Pro Leu Ala Lys Ala Asp Glu
             340                 345                 350

Thr Val Ser Ile Ala Gly Lys Cys Cys Glu Ser Gly Asp Met Leu Ile
             355                 360                 365

Trp Asp Leu Pro Leu Pro Lys Ala Asp Ser Asp Asp Ile Leu Ala Val
```

|  | 370 |  |  |  | 375 |  |  |  | 380 |  |  |  |  |
|---|---|---|---|---|---|---|---|---|---|---|---|---|---|
| Phe 385 | Cys | Thr | Gly | Ala | Tyr 390 | Gly | Tyr | Ser | Met | Ala 395 | Asn | Asn | Tyr | Asn | Arg 400 |
| Ile | Pro | Arg | Pro | Ala 405 | Val | Val | Phe | Val | Glu 410 | Asn | Gly | Glu | Ser | Met 415 | Leu |
| Val | Val | Lys | Arg 420 | Lys | His | Met | Arg | Thr 425 | Ser | Ser | Ala | Met | Ile 430 | Cys | Leu |